(12) United States Patent
Malnou et al.

(10) Patent No.: US 8,679,465 B2
(45) Date of Patent: Mar. 25, 2014

(54) COSMETIC COMPOSITION FOR NAILS, FREE OF PHTHALATES, CAMPHOR AND AROMATIC SOLVENT

(75) Inventors: Alain Malnou, Routot (FR); Francisco Martinez, Chartres (FR)

(73) Assignee: FIABILA, Maintenon (FR)

( * ) Notice: Subject to any disclaimer, the term of this patent is extended or adjusted under 35 U.S.C. 154(b) by 2007 days.

(21) Appl. No.: 10/332,814

(22) PCT Filed: Jun. 11, 2002

(86) PCT No.: PCT/FR02/01987
§ 371 (c)(1),
(2), (4) Date: Jan. 13, 2003

(87) PCT Pub. No.: WO02/100322
PCT Pub. Date: Dec. 19, 2002

(65) Prior Publication Data
US 2003/0152535 A1    Aug. 14, 2003

(30) Foreign Application Priority Data

Jun. 12, 2001 (FX) .................................... 01/07702

(51) Int. Cl.
*A61K 8/00* (2006.01)
(52) U.S. Cl.
USPC ........................................................ 424/61
(58) Field of Classification Search
USPC ........................................................ 424/61
See application file for complete search history.

(56) References Cited

U.S. PATENT DOCUMENTS

| 4,820,509 | A | | 4/1989 | Yamazaki et al. | |
| 5,066,484 | A | * | 11/1991 | Castrogiovanni et al. | 424/61 |
| 5,145,671 | A | | 9/1992 | Castrogiovanni et al. | |
| 5,662,891 | A | | 9/1997 | Martin | |
| 6,355,261 | B1 | * | 3/2002 | Bonda et al. | 424/401 |
| 6,583,207 | B2 | * | 6/2003 | Stanhope et al. | 524/291 |
| 6,740,314 | B2 | * | 5/2004 | Socci et al. | 424/61 |
| 6,939,551 | B2 | * | 9/2005 | Amato et al. | 424/401 |
| 2003/0023112 | A1 | * | 1/2003 | Lang et al. | 560/90 |

FOREIGN PATENT DOCUMENTS

| EP | 0 455 373 | | 11/1991 |
| EP | 0 495 373 | A2 | 7/1992 |
| EP | 0 613 676 | A2 | 9/1994 |
| EP | 0 613 677 | A2 | 9/1994 |
| EP | 0 740 930 | A1 | 11/1996 |
| EP | 0 894 490 | A1 | 2/1999 |
| FR | 2 785 531 | | 5/2000 |
| WO | 98/20843 | | 5/1998 |

* cited by examiner

*Primary Examiner* — Anand Desai
*Assistant Examiner* — Melissa Mercier
(74) *Attorney, Agent, or Firm* — Young & Thompson

(57) ABSTRACT

The cosmetic composition for nails without phtalate, without camphor or aromatic solvent comprises:
   a principal cellulosic filmogenic polymer, preferably nitrocellulose,
   a diester of benzoic acid with a diol, as a plasticizer,
   and at least one additive resin.
This composition can be used as a colored nail polish or for providing an adherent layer or a clear finish layer.

15 Claims, No Drawings

COSMETIC COMPOSITION FOR NAILS, FREE OF PHTHALATES, CAMPHOR AND AROMATIC SOLVENT

The present invention relates to a cosmetic composition for the nails, without phtalates, without camphor and without aromatic solvents and its use as a colored polish or for processing with an adherent layer or with a clear finishing layer.

Typically, a formulation of nail polish comprises a basic filmogenic polymer, secondary polymers, one or more plastifiers and one or more solvents. The mixture can also contain pigments, suspension agents and additives such as anti-UV agents, wetting agents, hydrating agents and perfumes.

All these formulations seek to optimize characteristic such as: a well-rounded application, a short drying time and a very brilliant finish. The formulator thus tries to keep this appearance by giving the formulation also high resistance to radiation, to wear, to chipping, to detergents and to greases. This must result in good adherence and a good compromise between hardness and flexibleness of said polish.

Numerous solutions have been proposed to meet these various requirements. The principal problem to be solved is the plastification of the nitrocellulose which remains the principal resin used in nail polishes. These phtalates and camphor are good plasticizers, but must be replaced because of their toxicity. For identical reasons, the use of aromatic solvents must also be avoided.

The constraints on producing nail polishes without phtalates, without camphor, and without aromatic solvents, have as a result changed the balance and the compromise of these formulations. New plasticizers have been envisaged.

In patent applications EP-A-0 495 373, EP-A-0 613 676 and EP-A-0 613 677, the REVLON company discloses various di- and trimesters. In the application WO-A-9 820 843, the KIRKER company uses a specific plasticizer TXIB (2,2,4-trimethyl 1,3-pentanediol diisobutyrate). L'OREAL plasticizes nitrocellulose with cross-linked polyesters (EP-A-0 740 930) or uses a fluorinated citrate (FR-A-2 785 531).

Mixtures of plasticizers have also been proposed, for example a mixture of citrate and toluene sulfonamide (EP-A-0 894 490), a mixture of sucrose benzoate and sulfonamide (U.S. Pat. No. 4,820,509), or else a mixture of sucrose acetate isobutyrate, butyl benzylbenzoate and glyceryl tribenzoate (U.S. Pat. No. 5,662,891).

In his tests, to obtain the best compromise between hardness, flexibility, drying, adherence and durability, the applicant has discovered that benzoic diesters of diols can preferably replace the phtalates.

These plasticizers permit particularly having, with cellulosic derivatives, properties of brilliance, flexibility, hardness and adherence that are very interesting for nails.

To this end, the cosmetic composition for the nails according to the invention, without phtalates, without camphor nor aromatic solvents, comprises:
a) a principal cellulosic filmogenic polymer (A),
b) a diester (B) of benzoic acid with a diol,
  (i) the benzoic acid being either unsubstituted benzoic acid, or benzoic acid substituted by one, two or three groups selected from: —CN, —SCN, —NO$_2$, —CI, —Br, —F, —OCH$_3$, —OC$_2$H$_5$, —OC$_6$H$_5$, —CH=CH$_2$, a C$_1$-C$_6$ alkyle branched or not, —CH$_2$CH=CH$_2$, —NO$_2$, —NH$_2$, —OH, —SH and —SO$_2$NH$_2$
  (ii) the diol being selected from:
    linear diols of the formula HO—(CH$_2$)$_n$—OH (I) in which n is a whole number between 4 and 20
    diols of the formula HO—(CH$_2$)$_x$-M-(CH$_2$)$_y$—OH (II) x and y being whole numbers from 0 to 4
    M being an aromatic cyclic or a cycloaliphatic, if desired substituted with a linear or branched C$_{1-30}$ alkyl, or a

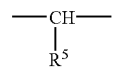

group
R$_5$ being a linear or branched alkyl radical of C$_1$ to C$_4$.
diols of the formula

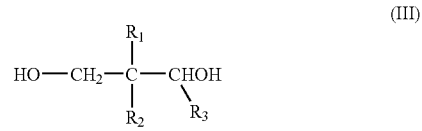

R$_1$ being hydrogen, or a linear or branched C$_1$-C$_4$ alkyl radical
R$_2$ being hydrogen, or a linear or branched C$_1$-C$_4$ alkyl
R$_3$ being a linear or branched C$_1$-C$_4$ alkyl radical
diols of the formula

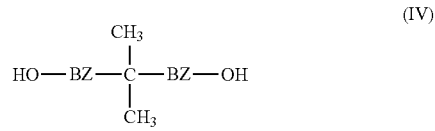

BZ being a benzenic radical
c) at least one additive resin (C).

Preferably, the principal filmogenic polymer A is selected from nitrocelluloses, cellulose acetobutyrates, cellulose acetopropionates, cellulose ethers and mixtures of these. The preferred filmogenic polymer is nitrocellulose, in particular nitrocellulose of about 12%, soluble in esters and insoluble in alcohols. The preferred grades of nitrocellulose comprise from 120 to 130 cellobiose units.

The cellulose acetobutyrates or acetopropionates are often used in clear nail polish as a finish or when a crystalline appearance is sought. Cellulose ethers, in particular ethyl cellulose, can complement the polymers A above, to increase the plasticity of the composition.

The new plasticizer B, a diester synthesized from a diol and a benzoic acid, has properties equivalent or superior to those of phtalates, particularly as to the high power of dissolving the cellulosic polymers, in particular nitrocellulose. The preferred diesters are hexane diol dibenzoates (in particular 1,6-hexandediol), trimethyl pentane diol (in particular 2,2,4-trimethyl 1,3-pentanediol) and methyl propane diol (in particular di tert-butyl benzoate of 2-methyl 1,3-propanediol).

Preferably, resin C is selected from thermoplastic (meth) acrylic resins, polyester resins with or without fatty acids but without phthalic acid, condensates of toluene sulfonamide, vinyl resins, polyurethane resins and mixtures of these latter.

The resins, obtained by condensation of ethyl toluene sulfonamide with formaldehyde or with an epoxy compound, are the preferred resins to improve adherence, by increasing the polarity of the film. These resins, rich in solids, increase the dry extract of the polish and give it a better covering power and a better shape.

Other resins could be used for the same purpose: acrylic resins and polyesters. In the category of acrylics, there are acrylics, methacrylics and styrene/(meth)acrylics. The less soluble resins are preferred (methyl and ethyl) of low molecular weight. Certain acrylic resins modified with siloxane or fluoride groups can be added for their surface tension and radiation resistance.

The polyester resins are condensations of polyacids with polyols or polyethylene/polypropylene glycols. These resins can be modified with synthetic fatty acids or monoglycerides of vegetable oils. Phtalic anhydride, isophtalic acid and terephtalic acid as the di-acid are of course unavailable for cosmetic compositions without phtalates.

There are used short chain resins in oils (about 30%) with castor oil or a synthetic fatty acid of the type Cardura E of Shell. The polyesters cited in the CTFA as copolymers of adipic acid/neopentylglycol/trimetallic anhydride or adipic acid/chdm/ma/neopentylglycol/trimetallic acid, are often used for nail polish compositions.

The preferred vinyl resins are high molecular weight copolymers of vinyl acetate/vinyl chloride partially hydrolyzed or vinyl terpolymer chloride/vinyl acetate/hydroxylethylacrylate. Polyvinyl butyrate can also be used.

Certain polyurethane resins, such as those described in the CTFA, give to nail polishes interesting properties, particularly as to the balance of hardness/flexibility.

Another plastifier can be added to dibenzoate B to modify a desired mechanical property. To this end, the composition according to the invention can also comprise other plastifiers and/or plastifying resins D of a molecular weight lower than about 1500.

Certain resins of low molecular weight are considered as external plasticizers because they plasticize the systems without dissolving the cellulosic resins. There can be cited polyester adipates, polyester sebacates or butyl acrylate resins.

Preferably, the composition according to the invention can also include at least one constituent E selected from colorants, pigments, fillers, suspension agents, anti-UV agents, antioxidant agents, active agents such as vitamins, proteins, vegetable, mineral and/or animal extracts, and any other conventional ingredient used in nail polish.

The pigments, fillers, artificial nacres, flakes and hard waxes such as modified or unmodified polypropylene waxes, are used to give color and decorative effects to the nail polishes.

Clays, hectorites or modified montmoriilonites, colloidal silicas, modified waxes, modified urea resins, serve in nail polishes as in paints, to modify the rheology of the systems so as to combine ease of application and holding of the particles in suspension.

Other additives such as silicone or fluorine compounds for surface tension and sliding properties, hard waxes of fine granulometry for anti-radiation characteristics, anti-UV compounds, wetting agents for the stability of the pigments, are added to modify certain quite specific properties.

Products with a therapeutic effect such as vitamins, antioxidants, oligo-elements, proteins, oils, can be introduced into certain nail polishes.

It has been discovered that the compositions whose sum of the components B+D (plastifiers) represents at least 2% by weight of the total composition, preferably about 6 to 12%, give the best results.

Similarly, the ratio between the filmogenic polymer A and the sum of the plasticizers B+D, A/(B+D) is preferably comprised between 0.2 and 5, preferably between 0.6 and 2.

Preferably, the composition according to the invention contains no formaldehyde. The resins are solubilized in non-irritating solvents, the composition comprising at least one solvent selected from ethyl acetate, butyl acetate, propyl acetate, di-isobutyl acetate, ethanol, isopropanol and mixtures of these. Other solvents such as diacetonealcohol, methoxypropanol and certain ketones can be added to adjust the speed of evaporation and drying.

Rheological agents that can be added to the composition according to the invention are preferably selected from modified clays of the montmorillonite or hectorite type, hydrophilic or hydrophobic pyrogenated silicas, modified waxes, modified urea resins and mixtures of these.

The production of these nail polishes is carried out in a conventional manner, according to the conventional operative mode comprising the following consecutive steps:

dissolution of the resins, plasticizers and various additives in solvents, dispersion of possible rheological agents in these solutions, dispersion of the pigments and coloring materials in these solutions, preparation of a base by mixing the solutions and possible complementary rheologic agents, preparation of colors by adding to this base pigment dispersions, nacres and flakes according to the colorometric standard, inspection of these products before packaging.

EXAMPLES

The present invention is illustrated by the examples of the following formulations (all the percentages are expressed by weight of the dry composition):

Example 1

Comparative

Formula according to the prior art with phtalate and camphor, without formaldehyde and without aromatic solvents

| Nitrocellulose (12.1%) | 10.6 |
|---|---|
| Polyester resin | 4.6 |
| Dibutyl phtalate | 4.8 |
| Camphor | 1.4 |
| Solvents | 75.2 |
| Stearalkonium hectorite | 0.9 |
| Pigments | 2.5 |

Example 2

Comparative

Formula according to the prior art with phtalate, camphor and formaldehyde, without aromatic solvents

| Nitrocellulose | 10.6 |
|---|---|
| Tosylamide/formaldehyde | 4.6 |
| Dibutyl phtalate | 4.8 |
| Camphor | 1.4 |
| Solvents | 75.2 |
| Stearalkonium hectorite | 0.9 |
| Pigments | 2.5 |

Example 3

Formula without phtalates or camphor, without formaldehyde and without aromatic solvents

| | |
|---|---|
| Nitrocellulose | 10.5 |
| Hexanediol dibenzoate | 8.1 |
| Acrylics | 1.5 |
| Polyester | 4.2 |
| Tosylamide epoxy | 3.0 |
| Solvents | 68.3 |
| Stearalkonium hectorite | 1.0 |
| Pigments | 3.4 |

Example 4

Formula without phtalates or camphor, without aromatic solvents and with formaldehyde

| | |
|---|---|
| Nitrocellulose | 10.0 |
| Hexanediol dibenzoate | 7.2 |
| Acrylics | 1.5 |
| Tosylamide/formaldehyde | 5.2 |
| Polyester | 3.0 |
| Solvents | 63.7 |
| Stearalkonium hectorite | 1.0 |
| Pigments | 3.4 |

Example 5

Formula without phtalates or camphor, without formaldehyde and without aromatic solvents

| | |
|---|---|
| Nitrocellulose | 14.5 |
| Trimethyl pentanediol dibenzoate | 13.1 |
| Solvents | 68.0 |
| Stearalkonium hectorite | 1.0 |
| Pigments | 3.4 |

The various nail polishes, having the above compositions, are prepared according to the conventional operative mode described in the introduction.

The characteristics of a nail polish being difficult to measure directly on the nails, tests are carried out by comparison on other surfaces such as glass or aluminum (qualicoat quality 5004 H 24).

The films are applied with the help of a Conway applicator to a wet thickness of 100 micrometers.

Drying is measured on a plate at 35° C. with a trace which leaves a rotating sphere on the nail polish applied wet at 100 micrometers on a Leneta type cardboard.

The physical tests are carried out after drying overnight at 20° C. or for 2 hours at 50° C.

The thicknesses are measured on aluminum according to the ISO 2360 standard.

The brilliance is measured with a brilliantometer at an angle of 60° according to the ISO 2813 standard.

The hardnesses are measured on glass with a persoz pendulum according to the ISO 1522 standard.

The flexibility of the film is tested on aluminum with a cylindrical 3 mm mandrel according to the ISO 1519 standard.

Tests of radiation, wear as well as strength under wet abrasion, can be carried out with an apparatus for the washability of paints as descried in the AFNOR T 30 082 standard.

Adherence is compared on glass with the quadrillage method, on a cutout film with a comb having teeth spaced 1 mm apart, according to tearing off of an adhesive strip (cf. ISO 2409 standard).

A final test of durability on the nails is arranged for a group of women to evaluate the brilliance, wear and chipping.

For formulations 1 to 5, the principal results are the following:

| | No. 1 | No. 2 | No. 3 | No. 4 | No. 5 |
|---|---|---|---|---|---|
| Drying | 4.25 min | 3.5 min | 2.5 min | 3.0 min | 3.5 min |
| Hardness | 260 sec | 230 sec | 200 sec | 195 sec | 210 sec |
| Adherence (0 to 5) | 0/1 | 0 | 0/1 | 0 | 0/1 |
| Flexibility (3 mm Cyl.) | Passing | Passing | Passing | Passing | Passing |
| Time on the nails | 2.9 days | 3.4 days | 3.1 days | 3.6 days | 3.5 days |

It has bee discovered that compositions 3, 5 and 4, respectively without formaldehyde and with formaldehyde, give results superior to the corresponding compositions 1 and 2, particularly as to the duration on the nails (at least +0.2 day, even +0.6 day for composition No. 5) with a shortened drying time.

Moreover, the compositions according to the invention including hexanediol dibenzoate or trimethyl pentane diol dibenzoate give more brilliant nail polishes.

The invention claimed is:

1. A nail polish composition, without phthalate, without camphor or aromatic solvent, comprising:
    nitrocellulose as a principal cellulosic filmogenic polymer (A);
    at least one additive resin (C);
    at least one solvent; and
    a plasticizer being a diester (B) of a diol and a benzoic acid;
    said benzoic acid being either unsubstituted benzoic acid, or benzoic acid substituted with one, two or three groups selected from the group consisting of: —CN, —SCN, —NO$_2$, —Cl, —Br, —F, —OCH$_3$, —OC$_2$H$_5$, —OC$_6$H$_5$, —CH=CH$_2$, a C$_1$-C$_6$ alkyl branched or not, —CH$_2$CH=CH$_2$, —NO$_2$, —NH$_2$, —OH, —SH and —SO$_2$NH$_2$;
    said diol being of the formula (III)

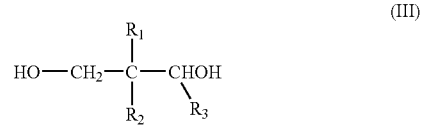

(III)

wherein,
R$_1$ being a linear or branched C$_1$-C$_4$ alkyl radical,
R$_2$ being a linear or branched C$_1$-C$_4$ alkyl radical,
R$_3$ being a linear or branched C$_1$-C$_4$ alkyl radical and, wherein the composition is without phthalic anhydride, isophthalic acid and terephthalic acid, without camphor or aromatic solvent.

2. The composition according to claim 1, wherein the resin (C) is selected from the group consisting of thermoplastic (meth)acrylic resins, polyester resins with or without fatty acids, toluene sulfonamide condensates, vinyl resins, polyurethane resins and mixtures thereof.

3. The composition according to claim 1, further comprising a constituent (E) selected from the group consisting of colorants, pigments, fillers, suspension agents, anti-UV agent, anti-oxidant agents, active ingredients, proteins, vegetable extracts, mineral extracts, and animal extracts.

4. The composition according to claim 1, characterized in that the sum of diester (B) and resins (D) represent 6% to 12% by weight of the total composition.

5. The composition according to claim 1, wherein the ratio of the filmogenic polymer (A) to the sum of the diester (B) and resins (D) is between 0.2 and 5.

6. The composition according to claim 1, wherein the composition does not comprise formaldehyde.

7. A nail polish composition, without phthalate, without camphor or aromatic solvent, comprising:
   nitrocellulose as a principal cellulosic filmogenic polymer (A);
   at least one additive resin (C);
   at least one solvent; and
   a plasticizer being a diester (B), said
diester (B) being dibenzoate of 2,2,4-trimethyl 1,3-pentane diol.

8. A nail polish composition, without phthalate, without camphor or aromatic solvent, comprising:
   nitrocellulose as a principal cellulosic filmogenic polymer (A);
   at least one additive resin (C);
   at least one solvent; and
   a plasticizer being a diester (B), characterized in that the diester (B) is 2-methyl 1,3-propanediol tert-butyl benzoate, and the composition is without phthalic anhydride, isophthalic acid and terephthalic acid, without camphor or aromatic solvent.

9. The composition according to claim 1, characterized in that the resin (C) is a condensation resin between ethyl toluene sulfonamide and formaldehyde or a condensation resin between ethyl toluene sulfonamide and an epoxy compound.

10. The composition according to claim 1, characterized in that the resin (C) is a polyester without phtalic acid.

11. The composition according to claim 1, further comprising at least one solvent selected from the group consisting of ethyl acetate, butyl acetate, propyl acetate, isobutyl acetate, ethanol, isopropanol and mixtures thereof.

12. The composition according to claim 1, further comprising rheological agents selected from the group consisting of modified clays of the montmorillonite or hectorite type, hydrophilic or hydrophobic pyrogenated silicas, modified waxes, modified urea resins and mixtures thereof.

13. A method of applying a nail polish composition according to claim 1, comprising the step of applying a single layer or several layers of said composition to said nails.

14. A method of applying an adherent layer of the composition according to claim 1 comprising applying said composition to a user's nails for primary adherence.

15. A method of applying the composition according to claim 1 to a user's nails, comprising applying said composition as a finishing layer or as an intermediate layer on said nails.

\* \* \* \* \*